United States Patent
Arnett et al.

(10) Patent No.: US 9,271,724 B2
(45) Date of Patent: Mar. 1, 2016

(54) MEDICAL DEVICE HAVING A POSITION INDICATOR

(75) Inventors: Jeffery Arnett, Gilbert, AZ (US); Neil Godara, Milton (CA); Robert Harrison, Milton (CA); Laura Man Yee Yu, Markham (CA)

(73) Assignee: ANCHOR OPTHOPEDICS XT INC., Mississauga, Ontario (CA)

( * ) Notice: Subject to any disclaimer, the term of this patent is extended or adjusted under 35 U.S.C. 154(b) by 617 days.

(21) Appl. No.: 13/589,151

(22) Filed: Aug. 19, 2012

(65) Prior Publication Data

US 2013/0046319 A1 Feb. 21, 2013

Related U.S. Application Data (60) Provisional application No. 61/524,765, filed on Aug. 18, 2011, provisional application No. 61/524,766, filed on Aug. 18, 2011, provisional application No. 61/561,486, filed on Nov. 18, 2011, provisional application No. 61/582,464, filed on Jan. 2, 2012, provisional application No. 61/586,287, filed on Jan. 13, 2012, provisional application No. 61/593,843, filed on Feb. 1, 2012, provisional application No. 61/597,449, filed on Feb. 10, 2012.

(51) Int. Cl.
*A61B 17/34* (2006.01)
*A61B 17/062* (2006.01)
*A61B 17/04* (2006.01)
*A61B 19/00* (2006.01)

(52) U.S. Cl.
CPC ............ *A61B 17/062* (2013.01); *A61B 17/0482* (2013.01); *A61B 2017/0475* (2013.01); *A61B 2017/0496* (2013.01); *A61B 2019/4857* (2013.01)

(58) Field of Classification Search
CPC ........... A61B 17/0469; A61B 17/0482; A61B 17/06; A61B 2019/4857; A61B 17/068; A61B 17/0682; A61B 17/0684; A61B 17/0686; A61B 17/072; A61B 17/07207
See application file for complete search history.

(56) References Cited

U.S. PATENT DOCUMENTS

| | | | |
|---|---|---|---|
| 2008/0103491 A1* | 5/2008 | Omori et al. | 606/1 |
| 2010/0087857 A1* | 4/2010 | Stone et al. | 606/232 |
| 2011/0022063 A1* | 1/2011 | McClurg et al. | 606/145 |

* cited by examiner

*Primary Examiner* — Jonathan W Miles
(74) *Attorney, Agent, or Firm* — Nir Lifshitz; Glen Arnold (57) ABSTRACT

A medical device is described, the medical device comprising a moveable member, moveable between a first position and a second position; an actuating member coupled to the moveable member, directly or indirectly, for manipulating the moveable member, that is for causing the movement of the moveable member; and an indicator coupled, directly or indirectly, to the actuating member, said indicator having a first state and a second state; the indicator and actuating member being cooperatively operable such that the indicator automatically transitions between the first state and the second state to indicate advancement of the member to the second position from the first position upon a predetermined actuation of the actuating member.

15 Claims, 8 Drawing Sheets

MEDICAL DEVICE HAVING A POSITION INDICATOR

CROSS-REFERENCES TO RELATED APPLICATIONS

This application is a non-provisional of U.S. Provisional Patent Application No. 61/524,765, filed on 2011 Aug. 18, and is a non-provisional of U.S. Provisional Patent Application No. 61/524,766, filed on 2011 Aug. 18, and is a non-provisional of U.S. Provisional Patent Application No. 61/561,486, filed on 2011 Nov. 18, and is a non-provisional of U.S. Provisional Patent Application No. 61/582,464, filed on 2012 Jan. 2, and is a non-provisional of U.S. Provisional Patent Application No. 61/586,287, filed on 2012 Jan. 13, and is a non-provisional of U.S. Provisional Patent Application No. 61/593,843, filed on 2012 Feb. 1, and is a non-provisional of U.S. Provisional Patent Application No. 61/597,449, filed on 2012 Feb. 10.

Each of the aforementioned applications is incorporated herein by reference in its entirety.

TECHNICAL FIELD

The disclosure relates to a medical device, more specifically to a medical device having an indicator for indicating the position of a portion of the device.

SUMMARY

In one broad aspect, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

In one broad aspect, embodiments of the present invention include a medical device comprising: an actuator coupled, directly or indirectly, to a moveable member and being for actuating said movable member from a first position to a second position; and an indicator for indicating a position of said moveable member, said indicator being actuated by movement of said moveable member.

As a feature of this broad aspect, the indicator is configured to automatically transition between a first state and a second state upon a predetermined actuation of the actuator which moves said movable member from said first position to said second position.

The actuator, such as a trigger, may be coupled to the indicator directly or indirectly, for example via one or more additional components.

In some embodiments, the device further comprises a component for detachably coupling to the moveable member, wherein movement of the moveable member between the first position and the second position upon actuation of the trigger results in translation of the component between the first position and the second position; and wherein the change in the indicator between the first state and the second state indicates the translation of the component to the second position. In some examples, the component comprises a suture-carrying shuttle or suture trap, a suture or an anchor. In some examples, wherein the moveable member comprises an elongate member, the moveable member may be a needle or a stylet.

In some embodiments, the elongate member automatically returns to the first position after advancement to the second position upon release of the trigger. In one example, the indicator changes between the first state and the second state upon release of the trigger.

In some embodiments, the indicator may be a sensory indicator, such as a visual indicator, an audible indicator, or a tactile indicator. In some examples of a visual indicator, the indicator may be a mechanical indicator or an electronic indicator. In an example of a mechanical indicator, the indicator defines a proximal position wherein said indicator is in the first state and a distal position wherein said indicator is in the second state. In one example of an electronic indicator, the indicator comprises a light-emitting diode (LED). In an example of a tactile indicator, the indicator comprises a protrusion or projection, for example on a surface of the medical device, wherein the protrusion or projection may be retracted or otherwise repositioned upon transition from the first state to the second state.

In a further broad aspect, embodiments of the present invention include a medical device comprising: a needle; a trigger coupled to the needle for reciprocally translating the needle between a first position and a second predetermined position; and an indicator coupled to the trigger, said indicator having a first state and a second state; wherein said indicator automatically transitions between the first state and the second state to indicate advancement of the needle to the second predetermined position from the first position upon actuation of the trigger.

In an additional broad aspect, embodiments of the present invention comprise a medical device comprising: a device proximal portion and a distal tip coupled to the proximal portion; an elongate member housed within the proximal portion; a suture trap for removably coupling to the elongate member; an actuating member for allowing reciprocal movement of the elongate member for translating the trap between a trap proximal position and a trap distal position; and an indicator having a first state and a second state; the actuating member and the elongate member being cooperatively coupled such that actuation of the actuating member advances the elongate member for transferring the trap to the trap distal position, whereby the indicator automatically transitions from the first state to the second state.

In an example of this broad aspect, the first actuation of trigger allows the trap to automatically engage with the device distal tip. In a further example, the second actuation of the trigger allows the trap to automatically disengage with the device distal tip.

In some embodiments, the indicator is housed within the device proximal portion. In one example, the device proximal portion comprises a first aperture and a second aperture and wherein said indicator is visible from a first aperture in said first state and said indicator is visible from a second aperture in said second state.

In one example, the indicator automatically transitions between the first state and the second state upon actuation of the trigger. In a further example, the indicator automatically moves between the first state and the second state upon release of the trigger.

In some embodiments, the indicator serves as an indication of the completion of one or more steps of a multi-step medical procedure.

BRIEF DESCRIPTION OF THE DRAWINGS

In order that the invention may be readily understood, embodiments of the invention are illustrated by way of examples in the accompanying drawings, in which.

DETAILED DESCRIPTION

Certain medical procedures require the use of a medical device including a moveable portion or member that is translated or manipulated during the course of the medical procedure. Oftentimes, the position or location of the moveable portion once it has been translated or manipulated is not visible to the practitioner, either directly or via a medical imaging modality. In some specific applications, such as with procedures utilizing suture passing instrumentation to blindly pass a suture or suture retaining component through a tissue and back, it is desirable for a user to be aware of when the moveable portion has reached a position, relative to another portion of the device, for operably engaging with that other portion of the medical device.

For example, medical procedures involving the passage of suture may require capture or retrieval of the suture or a suture carrying component from a side of the tissue opposite a user. In some such cases, it would be beneficial for a user to be made aware when a suture retrieval component has reached a position whereby the capture of the suture (or suture carrying component) may be achieved.

In the past, certain devices have incorporated manual actuators for engaging or coupling components of a medical device, wherein the actuators include indicia indicating that the components have been coupled or decoupled. Such devices require manual assessment by a practitioner that the components of the medical device are in a position to be coupled, after which the actuator is manipulated to couple the components and indicate the coupling.

The present inventors have discovered and reduced to practice several embodiments of means for indicating a position of a portion or component of a medical device during use. Such embodiments are particularly useful and advantageous, for example, when the position or location of the portion or component is hidden from a user's view and/or when the portion or component are not amenable to visualization using an imaging modality (or when such imaging is unavailable to a user). Exemplary embodiments of the present invention provide an automatic mechanism for a medical device that is operable to provide an indication to a user, for example a sensory indication such as an audible or visual indication, when the portion or component of the medical device has, for example, been positioned at a certain location, has been moved or translated by a certain distance or amount or has reached a certain location relative to another component of the medical device.

Embodiments of the present invention avoid manual assessment of whether a moveable portion of the medical device has reached a desired position. The moveable member is coupled to the actuator so that the actuator serves to advance the moveable member from a first position to a second position, whereby, upon the moveable member reaching the second position, the indicator automatically transitions to its second state. In some such embodiments, incomplete actuation of the actuator does not fully advance the moveable member to the second position and does not result in a change of state of the indicator.

In one broad aspect, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In one embodiment of the present invention a device 100 is disclosed that allows for access to a region of tissue, such as for example, to puncture tissue and/or to deliver an article within a region of tissue. The device 100 comprises a member which may be moveable between a first position and a second position, for example the member may be moveable between a proximal position and a distal position. In a specific example, the member is moveable from a proximal position to a distal position and is retractable from the distal position to the proximal position. The moveable member may be an elongate member such as a needle 116 that may be housed within a device proximal portion 14. The device 100 may comprise an actuator (such as a trigger 218 shown in shown in FIG. 1) for advancing the needle 116 with respect to a proximal portion 14 of the device 100. As the trigger 218 is actuated, the needle 116 translates longitudinally from the proximal portion 14 of device 100 towards a distal portion of the device such as a distal tip 12 and it may puncture a region of tissue as it is advanced. In other words the needle 116 is advanced in a direction along the longitudinal axis of device 100. In one example, the needle 116 is a reciprocating needle which is advanced towards the distal tip 12 upon actuation of the trigger 118 and retracted proximally back towards the proximal portion 14 of the device when the trigger is released. In some embodiments, the moveable member is an elongated member that may comprise a stylet and/or needle. In some examples, the moveable member may be configured to be coupled to a component in order to carry the component and deposit it within the tissue. Some examples of components include but are not limited to a suture, a shuttle carrying a suture, a suture trap or an anchor. In some examples, the moveable member may itself comprise a component, i.e. the component may be a portion of the moveable member.

Figure 2A:
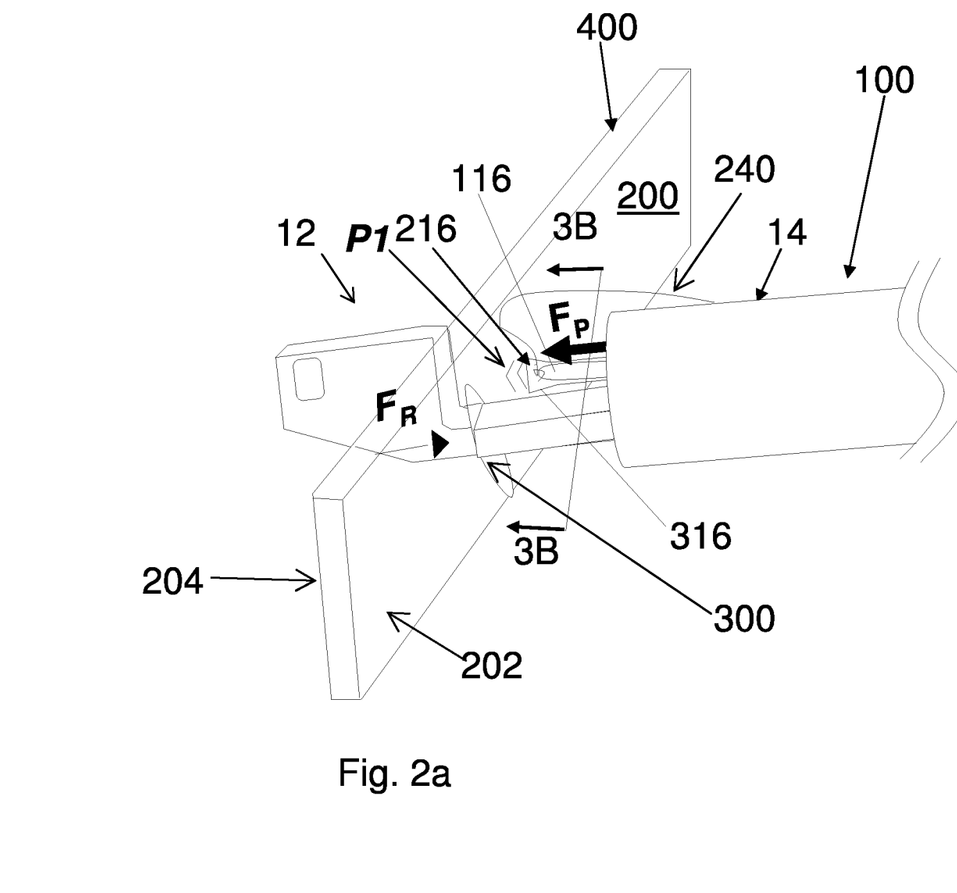
FIG. 2a is an illustration of a method in accordance with an embodiment of the present invention.
Figure 2B:
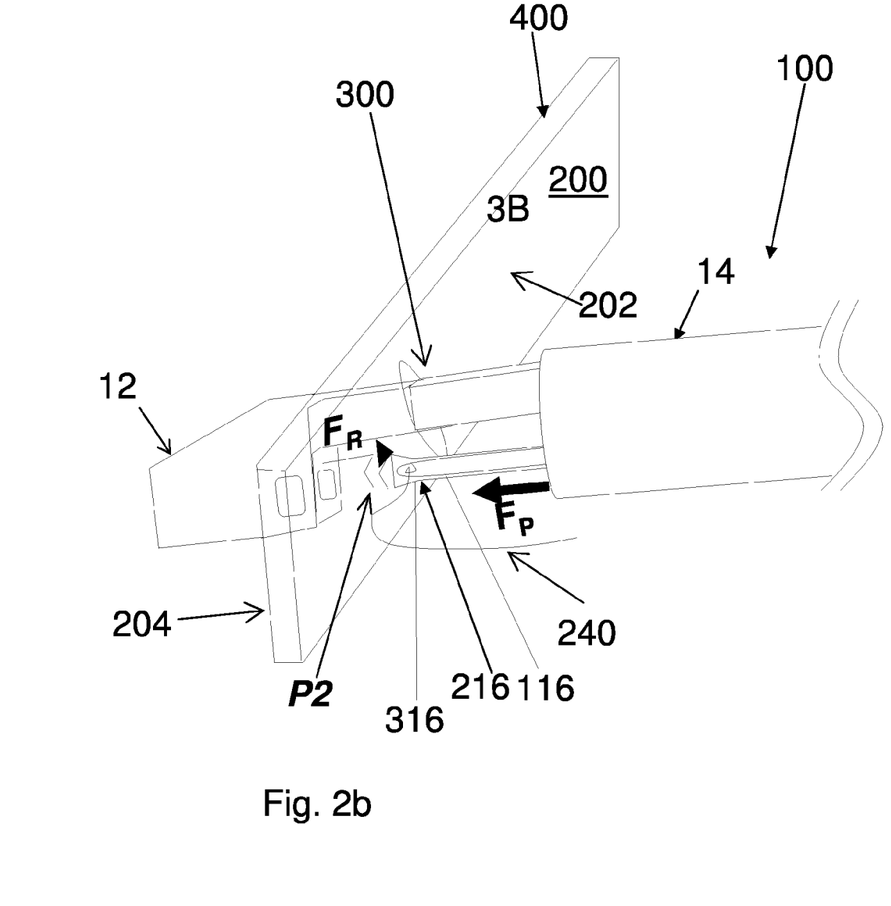
FIG. 2b is an illustration of a method in accordance with an embodiment of the present invention.

In one embodiment, the device 100 may be used to repair a defect within a region of tissue within a patient's body. For example, as illustrated in FIG. 2, the device 100 may be used to access a defect 300, a puncture may be created in the region of tissue adjacent the defect using the moveable member and delivering an article/component through the puncture in order to repair the defect. The device 100 is inserted at the site of a defect 300, as illustrated in FIGS. 2a and 2b, to allow the moveable member which may be a tissue puncturing member to be passed from the proximal side of the tissue 200 (for example, the external surface of the tissue), to the distal side of the tissue 200 (for example, the internal surface of the tissue). In one example, the tissue puncturing member is a needle/trap assembly 216. In another example, the tissue puncturing member is a needle 116. A tissue supporting member may be positioned through the defect on the distal side of the tissue adjacent the tissue distal surface 204 and may facilitate puncturing of the tissue using the tissue puncturing member. A desired first puncture site P1 is defined at some distance from the defect 300.

In one example of this method, the tissue puncturing member further allows an article/component to be carried from the proximal side of the tissue to the distal side of the tissue, for example, to repair the defect 300. In some embodiments, the tissue puncturing member such as needle 116 itself carries the article/component from the proximal to distal side of the tissue while puncturing the tissue. In other embodiments, the tissue puncturing member creates a puncture to allow access for the delivery of an article/component therethrough. In one example, the tissue puncturing member comprises a needle/trap assembly 216 and the article/component for repairing the defect is a suture 240. In another example, the article/component for repairing the defect is an anchor which may be coupled to or be a part of the moveable member which may be an elongate member such as needle 116. In one specific example of a method of repairing a defect, a needle/trap assembly 216 is used to pass a suture 240. The suture 240 is coupled to the trap 316 of the needle/trap assembly 216. As the needle/trap assembly 216 of device 100 is advanced against the tissue it applies a force against the proximal surface 202 of the tissue in order to puncture the tissue near the defect 300 at the desired puncture site P1.

Figure 1:
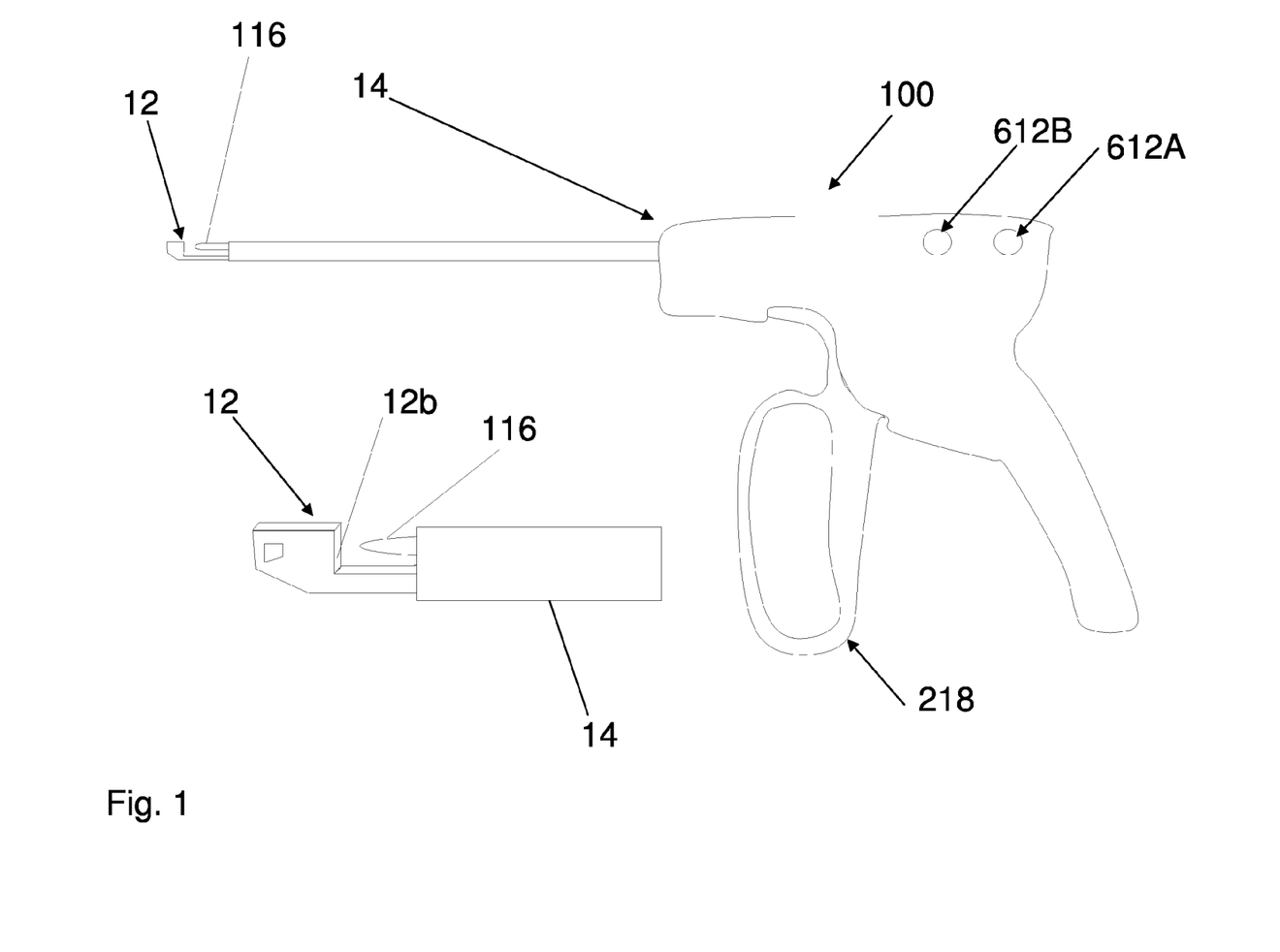
FIG. 1 is a view of portions of a device in accordance with an embodiment of the present invention.

As shown in FIG. 1, a trigger 218 is actuated to advance the tissue puncturing member such as the needle/trap assembly 216 from its first position to a second desired predetermined position such that it pierces the tissue 200. The tissue puncturing member may aid in passing a suture 240 from the proximal side of the tissue 200 to the distal side of the tissue 200. The tissue on one side of the defect may be punctured first as shown by puncture site P1 to pass a suture through the tissue. In one specific example, the distal tip 12 of device 100 defines a receiving chamber. The receiving chamber may be tapered distally to limit the distal movement of the needle/trap assembly 216 within the receiving chamber as the needle/trap assembly 216 is advanced. The trigger 218 is actuated to advance the needle/trap assembly 216 through the tissue 200 at the puncture site P1 such that it translates from the proximal side of the tissue and is received within the needle receiving chamber on the distal side of the tissue. Thus, the trap 316 carrying suture 240 allows the suture 240 to be positioned on the distal side of the tissue. The trap may then engage with the needle receiving chamber. The needle 116 may then be automatically retracted to its first position.

As illustrated in FIG. 2b, the device 100 may then be rotated and the position of the device 100 adjusted to allow suture 240 to be passed through a second segment, portion or flap of tissue on the other side of the tissue. In order to close the defect 300 the suture 240 may be passed through the tissue on the opposing side of the tissue 200 adjacent the puncture site P2. The trigger may be actuated again to allow the needle 116 to be re-advanced from its first position such that it punctures tissue at puncture site P2 on the other side of the defect. Thus needle 116 is advanced until it engages with the trap (with suture 240) which trap is then decoupled from the needle receiving chamber at the device distal tip 12. The needle 116 is then retracted automatically and the trap is retracted along with it. The suture 240 is passed from the distal side to the proximal side of the tissue through the second flap of the tissue. This allows the suture 240 to be passed through tissue on both sides of the defect to allow the two sides of the tissue to be approximated in order to close the defect.

In alternate embodiments, needle 116 may carry suture 240 directly to the other side of the defect, whereby suture 240 may be captured by trap 316 located on the other side of the defect.

In one example, the device 100 may comprise multiple needles 116 and corresponding needle receiving chambers within device distal tip 12. Similarly, the multiple needles 116 may be provided as multiple needle/trap 216 assemblies which may be used to pass a plurality of sutures. In one embodiment, the method of the present invention is used to treat a defect 300 within an annulus fibrosis tissue 400 of the intervertebral disc as shown in FIGS. 2A-2B. During treatment of such a defect within the intervertebral disc, a device 100 is inserted into the defect to allow a suture to be passed from the proximal surface 202 of the annulus tissue 400 to the distal surface 204 of the annulus tissue 400. In one example, a needle 116 and/or needle/trap assembly 216 is used to pass a suture 240. Thus in some embodiments, the suture 240 may be coupled to the needle and/or the needle/trap assembly 216. A suture is passed from the exterior annulus fibrosis to the inner annulus fibrosis and may be used to repair the defect 300 within the annulus tissue 400 using techniques known in the art.

In accordance with an embodiment of the present invention, an indicator may be provided that is associated with the device 100 that allows a user to ascertain if the first step has been successfully completed, i.e. This may allow the user to determine if the needle and/or needle/trap assembly 216 has deposited or transferred a component such as a suture 240 to the desired tissue location such as site P1. Depending on the indication received, the user may decide to proceed with the next step and re-advance the needle to deposit the suture through or at another desired location such as site P2. Conversely, if the first step was not successful, the user may decide to repeat it and may attempt to re-advance the needle 116 and/or needle/trap assembly 216, far enough to deposit the suture in the vicinity of the first desired location such as site P1.

Thus, as described herein above, the needle aids in passing the suture through one side of the defect (P1) and then the other side of the defect (P2) in order allow the two sides to be approximated to close the defect. Thus, an indicator may be used that provides an indication when the needle/suture assembly 216 is advanced far enough through one side of the defect (P1) such that the trap engages with the distal tip 12. The indication may be provided through the indicator moving into its second state from its first state. Thus when the needle automatically retracts to its original position without the trap, the indicator functions to provide an indication that the trap has successfully deposited the suture 240 where it is needed.

The user may then proceed with the second step. The trigger 218 may be re-actuated after the device is adjusted to allow the needle to puncture through the tissue 200 on the second side of the defect [site (P2)]. The needle is advanced again until it engages with the trap, allowing the trap to disengage from the distal tip. The needle is automatically retracted and the trap is consequently retracted along with the needle. The indicator automatically moves back to its first state from the second state, indicating that the trap has been successfully picked up and the suture has been threaded through tissue 200 on both sides of the defect, allowing the defect to be approximated.

Figure 3:
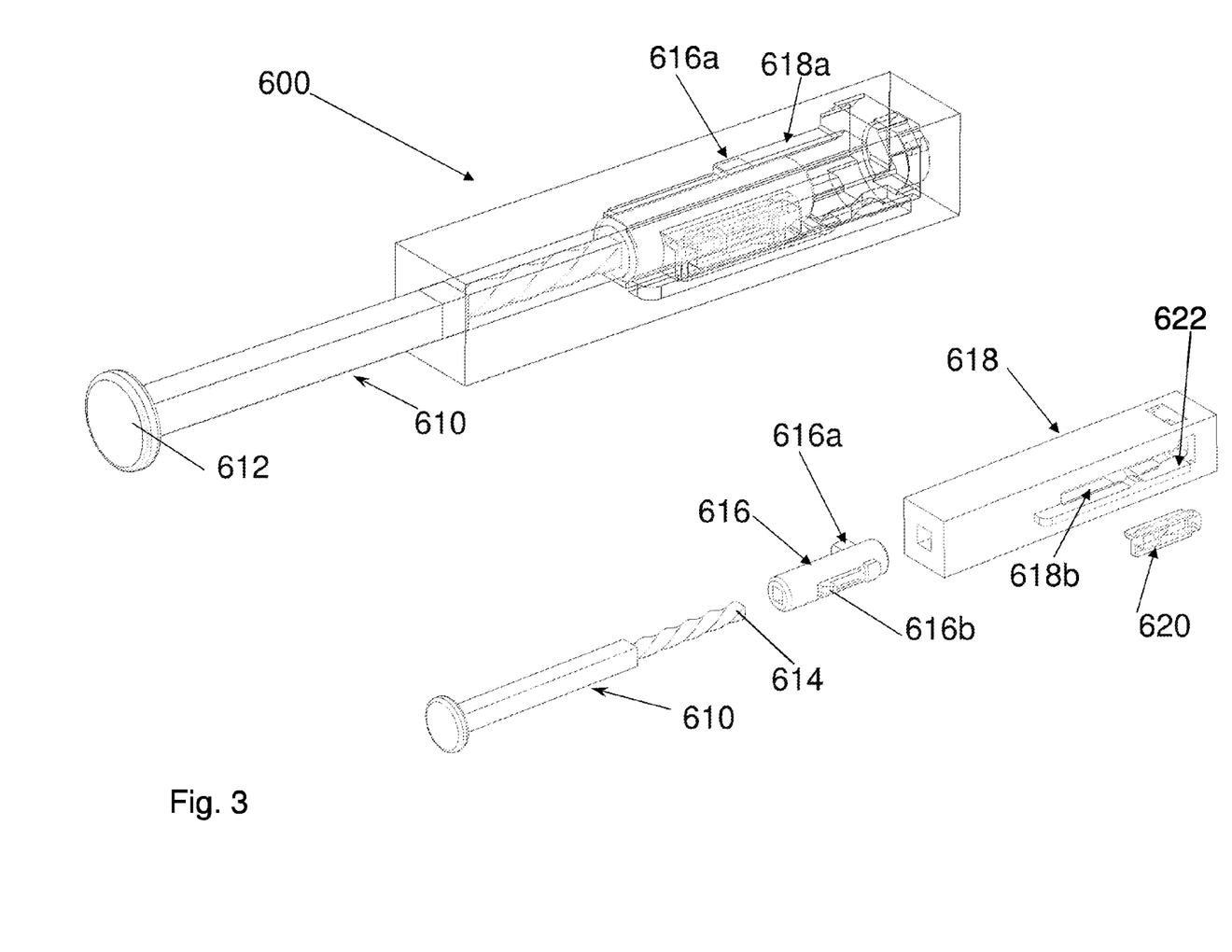
FIG. 3 illustrates a device in accordance with an embodiment of the present invention.

In one embodiment of the present invention, a device 100 is positioned within a region of tissue within the patient's body. The device 100 has a trigger 218 which allows advancement of a needle 116 to allow puncture of the tissue and to allow a suture to be deposited within the tissue, for example using a trap, in order to repair a defect 300 within the tissue. Referring now to FIG. 3, when the trigger 218 is actuated to advance the needle 116, an indicator 612 may be used to indicate if the trap carrying the suture has been captured at the distal tip 12 of the device 100. This may provide a positive indication of trap capture at distal tip 12 and of the suture being passed successfully through the tissue 200.

In one embodiment, the indicator 612 has two states, a first state when the indicator is in its initial proximal position and a second state when the indicator is in its distal position. In one example, the indicator 612 is coupled to a proximal end of a rod 610 having a helical thread or helix 614 that can co-operatively engage with threads on the inside of a hub 616 of the needle 116 (the needle 116, not shown, extends distally from the needle hub 616). The rod 610 is actuated using a trigger 218. In another example, the indicator 612 is a part of a gear rack which co-operatively engages with a geared portion of the trigger 218. The gear rack is slidable along the housing 618 and is coupled to the rod 610.

When the trigger 218 is actuated, the rod 610 advances and the needle hub 616 translates with it, which in turn advances the needle 116 in order to puncture tissue 200 at site P1. The trap 316 may be then coupled to the distal tip 12. The indicator mechanism is associated with the threading of the helix 614 inside the threaded portion of the hub which shortens the exposed portion of rod 610 (i.e. portion of rod 610 that is exposed outside the hub 616 which effectively shortens the rod 610). Thus, when the trigger 218 is released, the hub 616 with the shortened rod 610 is retracted, which results in the indicator 612 (which may be a part of the gear rack coupled to rod 610) being positioned distal to the initial indicator position, and is now in its second state. Thus, in one example, upon actuation of the trigger and subsequent release of the indicator 612, the indicator 612 changes from its first state to its second state. After the actuation of the trigger, the needle 116 may be retracted to its original position. The trigger 218 is then re-actuated. Once the trigger is pressed the rod 610 travels distally and allows the needle 116 to puncture through tissue at site P2. The needle continues to advance and the needle 116 may then re-couple to the trap 316. When the trigger 218 is released, the helix 614 unthreads and lengthens to its original position, which is the indicator 612 proximal position. Thus, the indicator reverts to its first state. In addition, in some embodiments, when the trigger 218 is released, the needle 116 and trap 316 (coupled to the needle 116) return to their initial proximal positions.

The indicator 612 is indicative of needle advancement and/or retraction as well as the position of the trap 316. When the trigger 218 is first actuated, the threading of the helix 614 inside the hub 616 results in shortening of rod 610 and also results in the coupling of the trap 316 within the device distal tip 12 and the uncoupling of the trap 316 from the needle. Thus when rod 610 is retracted, the indicator 612 in its distal position indicates transfer of the trap 316 from the needle to the distal tip 12 and indicates that the trap 316 position is distal. Similarly, when the trigger is re-actuated the unthreading of the helix 614 as the trigger is released results in lengthening of rod 610 and results in decoupling of the trap 316 from the device distal tip 12 and re-coupling of the trap 316 to the needle 116. Thus, when rod 610 is retracted, the indicator 612 in its proximal position indicates transfer of the trap 316 from the distal tip 12 to the needle 116 and indicates that the trap 316 position is proximal.

Alternatively, the trap 316 may be initially positioned at the device distal tip 12 in the trap distal position. In such an embodiment, a first actuation of the trigger 218 allows advancement of the needle 116 to capture or retrieve the trap 316 from the trap distal position to transfer the trap 316 to the trap proximal position and concurrently allows the indicator 612 to automatically move or change from the first state to the second state to indicate that the trap 316 is now in its proximal position. In other words, the first actuation of trigger 218 allows the trap 316 to automatically disengage with the device distal tip 12 and coupled with the needle 116. The trap 316 may then retract with the needle 116 as the trigger 218 is released. A second actuation of the trigger 218 allows advancement of the needle 116 to return the trap 316 into the trap distal position, i.e. the second actuation of the trigger allows the trap 316 to automatically engage with the device distal tip 12. Concurrently, the second trigger actuation allows the indicator 612 to automatically revert from the second state to the first state to indicate that the trap 316 is in its distal position.

In one specific example of this embodiment described above, the indicator 612 is coupled to the trigger 218 via rod 610. The rod 610 is receivable within a needle hub 616. The rod 610 has a helical thread 614 along a portion thereof, which co-operatively engages with a corresponding thread within the needle hub 616. In the initial starting position the indicator 612 (which may be a part of the gear rack coupled to the rod 610) may be visible through a first aperture 612A within the device proximal portion 14, which defines the indicator 612 in its first state. Thus, when the trigger 218 is actuated, the rod 610 is advanced which in turn advances the needle hub 616 causing the needle 116 to advance in order to puncture the tissue 200. The needle hub 616 resides within a housing 618 which is fixed within the proximal portion 14 of the device.

Figures 4A, 4B:
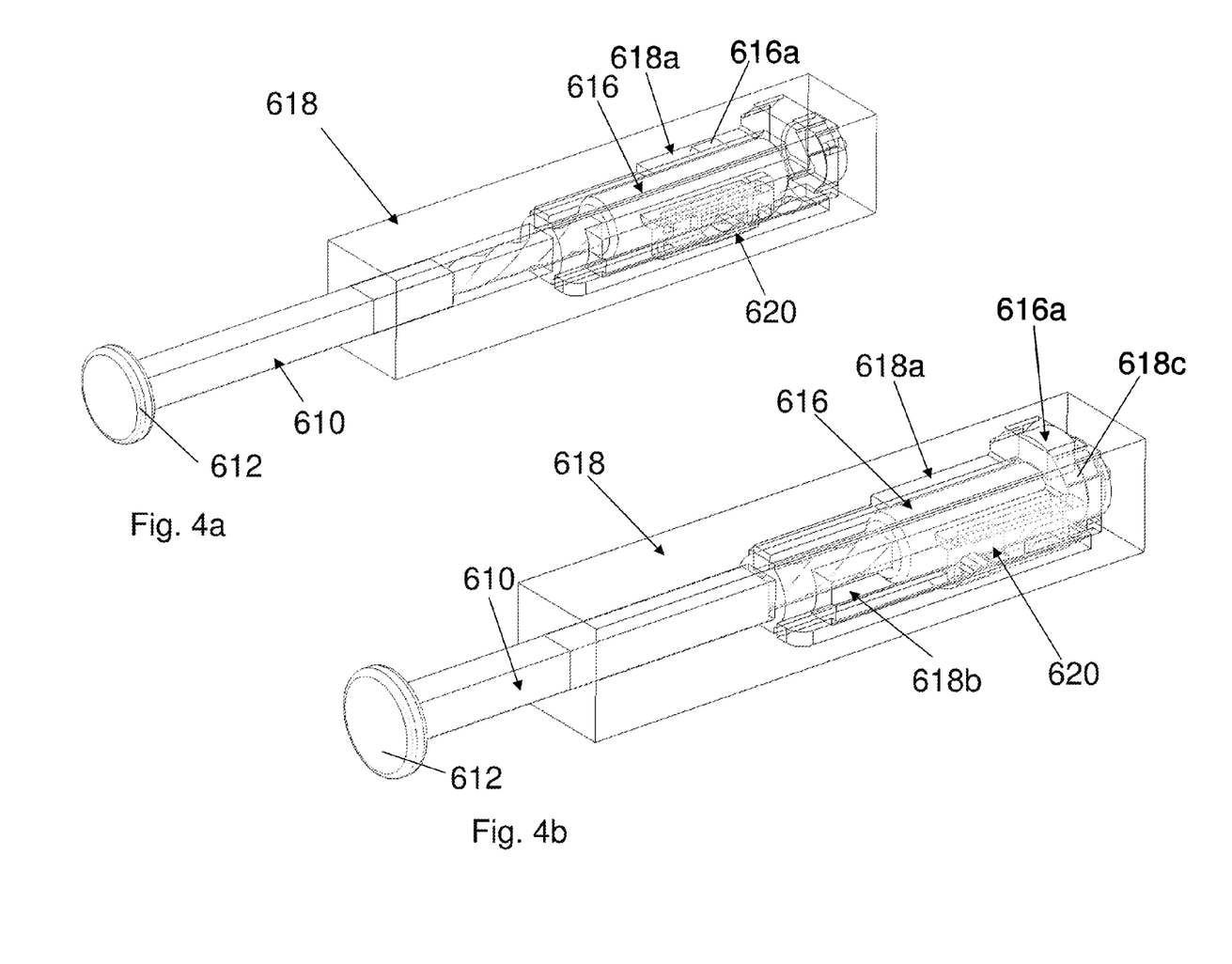
FIG. 4a-4g illustrate operation of a device, in accordance with an embodiment of the present invention.

As shown in FIG. 1 and FIG. 4a, the indicator 612 is initially in its proximal position 612A, when the trigger 218 is not depressed. The helical thread 614 is in its fully retracted position. The device 100 provides a mechanism that enables the needle hub 616 to translate within the housing 618 which allows advancement of the needle 116 from the initial or first needle position. In one specific example, as mentioned above, the trigger 218 has a geared portion that co-operatively engages with the gear rack (not shown) that is slidable along the housing 618 and is coupled to the rod 610. The trigger 218 is coupled to a biasing mechanism such as a spring biased mechanism. When the trigger 218 is in a neutral position, the spring is held against the bias. As the trigger is actuated, the geared portion of the trigger 218 advances the gear rack which further exerts a force against the spring bias. The rod 610 coupled to the gear rack translates distally causing the needle hub 616 and consequently the needle 116 to translate distally with respect to the housing 618. The hub 616 comprises a needle hub tab 616a that rides in a slot 618a within the housing 618. Due to the engagement of the needle hub tab 616a within the housing slot 618a, only translation of the hub 616 is permitted as shown in FIG. 4a. Since the hub 616 cannot rotate, the helical thread 614 of rod 610 pushes the hub 616 as the rod 610 is advanced. (Additionally, a snap tab 616b on the hub pushes a lifter 620 forwards, the lifter 620 allows the hub to retract back when the trigger 218 is released). In one example, the needle 116 punctures through site P1 as the hub is advanced.

Figures 4C, 4D:
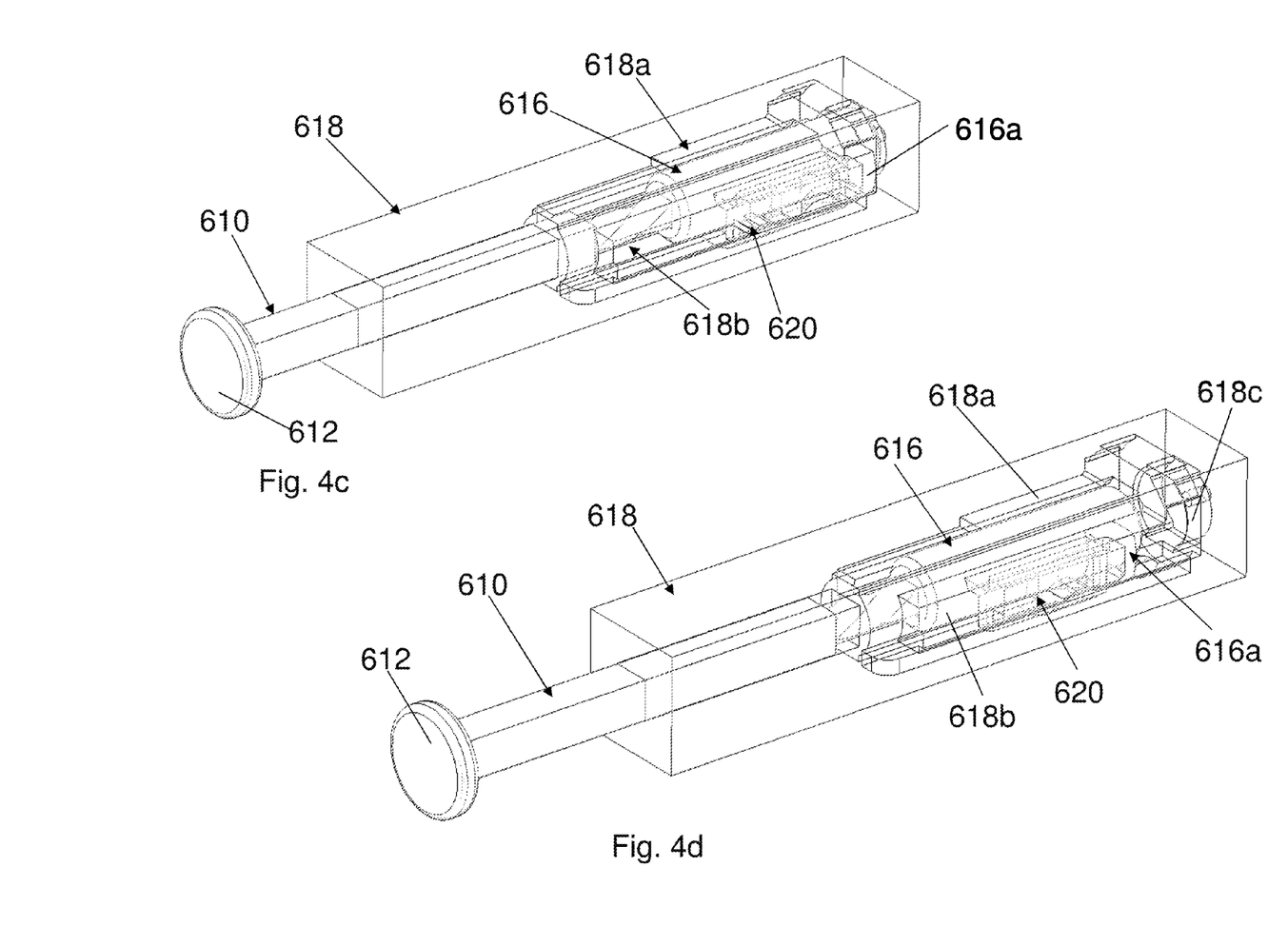

Once the hub 616 has translated maximally within the housing 618, the needle 116 is in the second needle position which is the desired predetermined position of the needle 116. The helical thread 614 threads into the corresponding thread of the hub 616. This causes the hub to rotate, allowing the hub 616 to screw onto or thread onto the rod 610, which shortens the length of the rod 610 that is outside the hub 616 as shown in FIGS. 4b and 4c. The hub tab 616a rotates within rotational slot 618c within the housing. When the trigger 218 is released, the biasing mechanism, such as the spring biased mechanism automatically urges the gear rack and thus rod 610 proximally towards the bias back towards the needle first position. The rotation of the rod 610 is restricted again using housing slot 618b. Thus as the trigger is released, the helical thread 614 of the rod 610 retracts, and since the hub 616 cannot rotate, the helical thread 614 pulls the hub proximally. Thus, the hub tab 616a rides within slot 618b which prevents the helical thread 614 from unthreading from the hub 616, and when the rod 610 is retracted, only a short length is exposed outside the hub 616 (as shown in FIG. 4d) and the indicator 612 (which may be a part of the gear rack coupled to rod 610) is now in its second state and is visible through the second aperture 612B. (The position of the indicator 612 as shown in FIG. 4c upon full actuation of the trigger 218 is distal of the position of the indicator in FIG. 4d, which shows the indicator in its second state). In one specific example, a trap 316 that is carried by the needle 116, is deposited at the distal tip 12 as the hub 616 and needle 116 rotate during needle advancement. Thus, the trap 316 is coupled to the distal tip 12 through a rotational mechanism. In summary, as the needle 116 advances with the trap 316 (which carries the suture) it punctures through the tissue 200 at site P1. Once the hub 616 advances, the needle 116 punctures through a tissue flap on a first side of the defect 300 as shown in FIG. 2a and is then coupled to the distal tip 12.

The hub 616 automatically retracts when the trigger is released and the indicator 612 automatically moves to its second or distal state (i.e. indicator 612 is visible through the second aperture 612B). This may be indicative of the trap 316 being received at the distal tip 12 and/or successful placement of suture through the tissue at site P1. In other words, the indicator 612 indicates to the physician that the needle 116 has been advanced far enough to a predetermined desired location to allow the trap 316 to be captured by/or engaged with the distal tip 12. In some embodiments, the indicator 612 may additionally indicate that the needle 116 has additionally been rotated fully after advancement to the predetermined desired location to allow the trap 316 to captured by/or engaged with the distal tip 12. Thus the physician has a positive indication that the suture was successfully deposited through the tissue flap along a first side of the defect 300 at site P1.

As described in the embodiment above, the retraction of hub 616 allows the indicator to move into its distal or second position. In one specific example, there is a snap arm 622 (shown in FIG. 3) on the housing 618 that prevents proximal retraction of the hub 616 when the trigger is released. Thus, in order to enable the hub 616 to retract back as the trigger is released, a lifter 620 is engaged with the hub to the hub snap tab 616b when the rod 610 is advanced, as shown in FIGS. 4a and 4b. When the trigger 218 is fully actuated, the lifter 620 translates with hub 616 to its distal most position pushing the snap arm 622 out of the way of the hub 616. This allows the hub 616 to translate back as the trigger 218 is released. The indicator 612 which is coupled to the hub 616 via rod 610 moves to its distal position indicative of suture being passed successfully through site P1 and trap being captured at the distal tip 12.

The physician then may reposition the device in order to allow the suture to pass through tissue 200 through site P2 on the other side of the defect 300. In one specific example, the device 100 may be rotated by 180° and the trigger may be re-actuated. When the trigger 218 is re-actuated the geared portion on the trigger 218 pushes the gear rack distally. Thus, as, shown in FIG. 4e, re-actuation of the trigger 218 allows the needle to advance, allowing the indicator 612 to advance from the indicator distal position. The rod 610 remains in its threaded position inside the hub 616 (i.e. with only a short/small segment of rod 610 being exposed outside the hub 616). When the hub 616 is advanced, the movement of the hub 616 is restricted to translational motion only as needle hub tab 616a translates along slot 618b. This allows the threaded helical thread 614 of the needle 116 to push the needle hub 616 distally allowing the needle to puncture through tissue along a second side of the defect at site P2. The needle 116 is received within the trap 316 that is engaged at the distal tip 12. Once the needle hub tab 616b has reached the end of the translation slot 618b, it then moves into the rotation slot 618c and rotation is then permitted. However, proximal translation of the needle hub 616 is prevented by the snap arm 622 on the housing snapping behind and abutting against the hub 616. In some embodiments, the lifter 620 remains in the distal position after having detached from the hub 616 during initial actuation of the trigger.

Figures 4E, 4F:
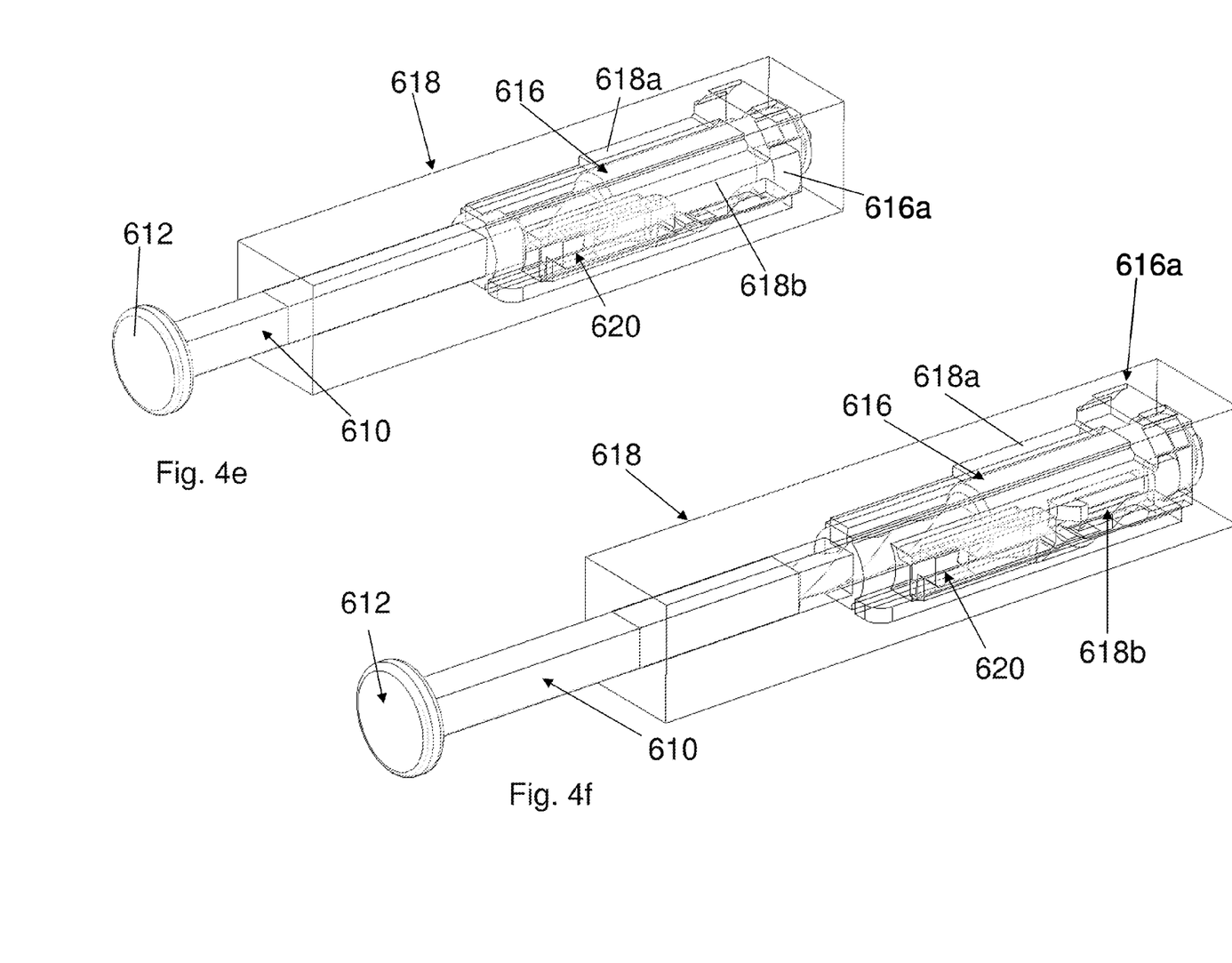
Figure 4G:
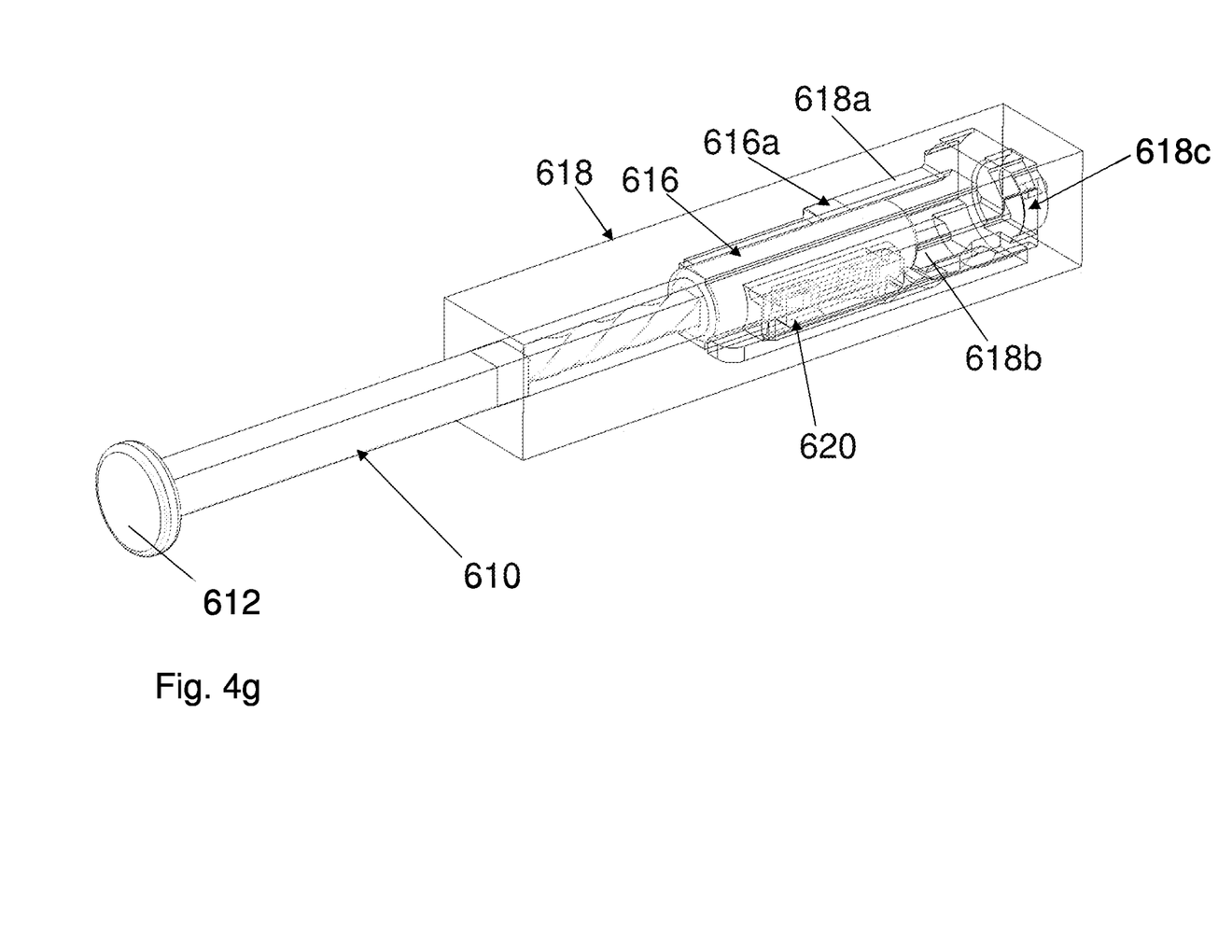

As the trigger 218 is released, the spring biased mechanism allows the trigger 218 to automatically retract proximally towards the bias. The geared portion of the trigger 318 causes the geared rack to translate proximally. The hub 616 unthreads from the helical thread on rod 610 causing the needle 116 to rotate, allowing the trap 316 to disengage from the distal tip 12, as shown in FIG. 4f. Thus the hub tab 616a is now located within the slot 618a and translation is now allowed. As the trigger is retracted further and as only translation is permitted, the helical thread 614 pulls the hub 616 proximally and hence the needle/trap assembly 216 along with it. Once the trigger has been fully released, the needle hub tab 616b has reached the end of the housing slot 618b and the needle/trap assembly 216 is fully retracted. The snap tab 616b on the hub 616 is deflected and snaps up, engaging the lifter 620 when it reaches full retraction. The indicator is now back in its original proximal position and is visible through the proximal aperture 612A, indicating that the trap is now in the proximal portion of the device and the suture has been successfully transferred through tissue site P2. Thus, the indicator 612 has moved to its first state Thus, in the example outlined above, the indicator 612 is a mechanical indicator and indication is provided through relative movement of the indicator 612 that is visible through the proximal or distal apertures 612A and 612B. Thus the indicator 612 functions as a visual indicator. In other examples, the indicator 612 may be an audible indictor or a tactile indicator.

Further details regarding a procedure utilizing an indicator, as well as examples of an audible indicator, are found in co-pending U.S. provisional patent application Ser. No. 61/597,449, filed 10 Feb. 2012, incorporated previously herein by reference in its entirety, as well as in co-pending PCT application serial number PCT/IB2012/054204, filed 17 Aug. 2012, incorporated herein by reference in its entirety.

In one embodiment, the indicator 612 may be a mechanical indicator as mentioned above but may not involve a rotational mechanism. In other words, the indicator 612 may be coupled to the needle advancement mechanism but may be independent from the needle/trap coupling and decoupling mechanism. In one embodiment, the indicator 612 is coupled to the trap delivery mechanism and the indicator 612 is capable of indicating both when the trap has either reached or been captured at the distal tip 12 and when the trap has either reached or is positioned at the proximal portion 14 of the device. In one embodiment, the indicator 612 may comprise a first state indicating the trap proximal position and a second state indicating the trap distal position. The indicator 612 for indicating the trap position may be for example coupled to the needle advancement mechanism, where needle advancement upon actuation of a trigger to a predetermined desired location, for example to the distal tip 12, is indicated by the indicator 612 moving into an indicator second state, which is indicative of trap 316 capture at the distal tip 12. Similarly, re-actuation of the trigger in order to re-advance the needle to the predetermined desired location may allow capture of the trap and may allow the indicator 612 to move to its original or first state, which is indicative of trap return to the trap proximal position.

In an alternative embodiment of the present invention, the indicator 612 may comprise an electronic indicator means that may be wirelessly or electronically coupled to the needle advancement mechanism or the trap coupling or decoupling mechanism (for detaching/attaching the trap 316 either to the needle 116 or the distal tip 12). As an example, a sensor may be coupled to the either the needle 116 or the distal tip 12 that detects the presence of the trap 316. More specifically, a contact sensor at the distal tip 12 may be coupled via a conductor wire to an indicator 612 which is in the form of a light emitting diode (LED). When contact between the trap 316 and the distal tip is made, the information from the sensor may be relayed to the LED which may light up (indicator second state) indicating that the needle has been translated to the predetermined desired position. The lit LED may also be indicative of the trap 316 being captured at the distal tip 12.

Thus, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A medical device comprising:
   a moveable member for transferring a component;
   an actuator coupled to the moveable member for actuating said moveable member from a first position to a second position; and
   an automatic indicator for indicating movement of said moveable member, the indicator having a plurality of states comprising at least a first state and a second state, said indicator being configured to automatically transition from said first state to said second state to indicate movement of said moveable member between said first and second positions sufficient to transfer the component;
   wherein said indicator is configured to remain in said second state following initial retraction of said moveable member from said second position and to automatically transition from said second state back to said first state when said moveable member is subsequently retracted from said second position upon re-actuation and release of said actuator.

2. The device of claim 1, wherein the actuator comprises a trigger.

3. The device of claim 2, wherein the moveable member automatically returns to the first position upon release of the trigger.

4. The device of claim 1, further comprising the component, the component operable to be detachably coupled to said moveable member, wherein movement of said moveable member between the first position and the second position upon actuation of the actuator results in translation of the component.

5. The device of claim 4, wherein the component comprises a suture trap.

6. The device of claim 4, wherein the component is selected from the group consisting of a suture and an anchor.

7. The device of claim 1, wherein the moveable member comprises an elongated member.

8. The device of claim 1, wherein said indicator is selected from the group consisting of a visual indicator, an audible indicator and a tactile indicator.

9. The device of claim 1, wherein said indicator is selected from the group consisting of a mechanical indicator and an electronic indicator.

10. The device of claim 1, wherein the indicator in the first state is positioned at a first location within the device and the indicator in the second state is positioned at a second location within the device.

11. The device of claim 10, wherein the position of the indicator serves as an indication of its change of state.

12. A medical device comprising:
    an elongate member;

a trigger coupled to the elongate member for reciprocally translating the elongate member between a first position and a second predetermined position; and an automatic indicator coupled to the trigger, said indicator having a first state and a second state;

wherein said indicator is configured to automatically transition between the first state and the second state to indicate advancement of the elongate member to the second predetermined position from the first position upon actuation of the trigger; and wherein said indicator automatically transitions from the second state back to the first state when said elongate member is re-advanced from the first position to the second pre-determined position upon re-actuation of the trigger.

13. A medical device comprising:

a device proximal portion and a distal tip coupled to the proximal portion;

an elongate member housed within the proximal portion;

a suture trap for removably coupling to the elongate member;

an actuating member for allowing reciprocal movement of the elongate member for translating the trap between a trap proximal position and a trap distal position; and an automatic indicator having a first state and a second state;

the actuating member and the elongate member being cooperatively coupled such that actuation of the actuating member advances the elongate member for transferring the trap from the trap proximal position to the trap distal position, whereby the indicator automatically transitions from the first state to the second state; and wherein said indicator automatically transitions from the second state back to the first state when said elongate member is re-advanced from the trap proximal position to the trap distal position upon re-actuation of the trigger.

14. The device of claim 13, wherein the indicator is housed within the device proximal portion.

15. The device of claim 14, wherein the device proximal portion defines a first aperture and a second aperture and wherein said indicator is visible from the first aperture in said first state and from the second aperture in the second state.

* * * * *